United States Patent [19]
Shaw

[11] Patent Number: 6,090,077
[45] Date of Patent: Jul. 18, 2000

[54] SYRINGE PLUNGER ASSEMBLY AND BARREL

[76] Inventor: Thomas J. Shaw, 1510 Hillcrest, Little Elm, Tex. 75068

[21] Appl. No.: 08/843,050

[22] Filed: Apr. 25, 1997

Related U.S. Application Data

[63] Continuation-in-part of application No. 08/537,242, Sep. 29, 1995, Pat. No. 5,632,733, which is a continuation of application No. 08/438,954, May 11, 1995, Pat. No. 5,578,011.

[51] Int. Cl.$^7$ ..................................................... A61M 5/00
[52] U.S. Cl. ........................... 604/195; 604/110; 604/218
[58] Field of Search ..................................... 604/195, 198, 604/263, 110, 187, 218, 227

[56] References Cited

U.S. PATENT DOCUMENTS

| | | | |
|---|---|---|---|
| 4,838,863 | 6/1989 | Allard | 604/110 |
| 4,838,869 | 6/1989 | Allard | 604/105 |
| 4,874,382 | 10/1989 | Lindeman et al. | 604/195 |
| 5,019,044 | 5/1991 | Tsao | 604/110 |
| 5,049,133 | 9/1991 | Pascual | 604/110 |
| 5,053,010 | 10/1991 | McGary et al. | 604/110 |
| 5,064,419 | 11/1991 | Gaarde | 604/195 |
| 5,084,018 | 1/1992 | Tsao | 604/110 |
| 5,090,962 | 2/1992 | Landry, Jr. er al. . | |
| 5,112,316 | 5/1992 | Venturini | 604/195 |
| 5,114,410 | 5/1992 | Batlle | 604/195 |
| 5,163,918 | 11/1992 | Righi et al. | 604/198 |
| 5,180,369 | 1/1993 | Dyszrz | 604/110 |
| 5,188,599 | 2/1993 | Botich et al. | 604/110 |
| 5,201,710 | 4/1993 | Caselli | 604/110 |
| 5,211,629 | 5/1993 | Pressly et al. | 604/110 |
| 5,304,138 | 4/1994 | Mercado | 604/110 |
| 5,324,265 | 6/1994 | Murray et al. | 604/110 |
| 5,346,480 | 9/1994 | Hess et al. | 604/198 X |
| 5,370,620 | 12/1994 | Shonfeld | 604/218 X |
| 5,376,080 | 12/1994 | Petrussa . | |
| 5,385,551 | 1/1995 | Shaw | 604/110 |
| 5,389,076 | 2/1995 | Shaw | 604/110 |
| 5,407,431 | 4/1995 | Botich et al. . | |
| 5,411,489 | 5/1995 | Pagay et al. | 604/218 |
| 5,505,703 | 4/1996 | Bartlett et al. | 604/110 |
| 5,527,286 | 6/1996 | Lekhgolts et al. | 604/110 |
| 5,613,952 | 3/1997 | Pressly, Sr. et al. . | |

FOREIGN PATENT DOCUMENTS 2197792  11/1986  United Kingdom .

*Primary Examiner*—John D. Yasko
*Attorney, Agent, or Firm*—Locke Liddell & Sapp, LLP

[57] ABSTRACT

A tamperproof retractable non-reusable syringe has a one piece hollow outer body with a barrel for a slidable plunger, a transition zone and a smaller diameter nose portion. An elongated needle holder and spring combination is installable from the rear of the outer body, guided into the nose portion and held by cooperating inwardly and outwardly facing surfaces oriented in the direction of retraction at the most constricted part of the transition zone where the nose begins. The plunger has an opening with a dislodgable stopper for receiving parts of the retraction mechanism. The stopper and the head of the needle holder are of significantly reduced diameter from the injection fluid chamber to resist blowing out prematurely. In one embodiment the head of the needle holder is surrounded by a separable retainer member which is slidingly removed by contact with the tip of the plunger after the stopper is mostly or fully removed to avoid cumulation of force required for retraction after the injection. In a second embodiment the head of the needle holder is clamped and held by constricting forces imposed by stress on the outer body induced by interference fit. Release occurs by slight expansion on the barrel by contact of the plunger tip with a small internal ramp in the outer barrel. Both embodiments have a plunger cap configured to enter an opening in the outer body to provide an additional tamperproof feature. The retraction cavity is provided with venting structures to assure that all uninjected fluid is retained within the syringe body.

41 Claims, 8 Drawing Sheets

SYRINGE PLUNGER ASSEMBLY AND BARREL

This is a continuation-in-part of patent application Ser. No. 08/537,242 now U.S. Pat. No. 5,632,733 filed Sep. 29, 1995 entitled Tamperproof Retractable Syringe which in turn was a continuation of Ser. No. 08/438,954 filed May 11, 1995, now U.S. Pat. No. 5,578,011 all by the same inventor for which benefit is claimed under 35 U.S.C. §120.

FIELD OF THE INVENTION

This invention relates to a medical device, and more particularly to a retractable syringe and components suitable for mass production and assembly having a low triggering force and high blowout pressure which is nonreusable after one use.

BACKGROUND OF THE ART

A major cause to the spread of AIDS in the general population is the presence of IV drug users who share and reuse hypodermic syringes to inject drugs. Infection can be spread from AIDS patients in hospitals and medical facilities through accidental needle sticks from needles used on infected patients. Used syringes with extended needles present a risk to medical personnel and sanitation employees and others in the disposal chain.

The gravity of the threat posed by AIDS and the fact that the main vector of the spread of the dreaded disease is through reuse of syringes by IV drug users has resulted in intense activity to develop the most practical, most reliable, easily assemblable, mass-producible syringe.

There are a number of syringes of different designs which have needles which will retract at the end of the injection cycle. Most of these have never reached the market because of various deficiencies. Prime among the usual deficiencies of the prior art are problems of complexity, reliability, cost and ease of use. The most commonly used syringes are 1 cc and 3 cc syringes which must be mass-produced at the rate of millions per day. Cost is a significant factor both in manufacture of the parts and assembly of the device. High speed production requires molds with 64 cavities or more to reduce unit cycle time. Therefore, molded structures within the barrel that require collapsing core pins such as are shown in much of the art are unlikely to be producible at competitive costs.

One of the problems of the prior art of retractable syringes is the sheer number and complexity of parts which must be formed and assembled. Other problems with the prior art are dependence on flexing or breaking of internal parts by the plunger in order to release the retraction mechanism and use of a diaphragm at the end of the plunger which must be penetrated by a needle holding member and spring. These structures present serious quality control and assembly problems. Small broken off pieces can present a risk of hang-ups. Hooks are often used to releaseably secure retraction mechanisms. Hooks present difficult holding and control problems, may cause retention of air bubbles upon filling and may be undesirably temperature sensitive.

The prior art frequently has a two-piece barrel in order to be able to assemble a retraction device in the nose. This requires at least an additional part and assembly step. It is still necessary to pass the sharp injection needle through a small opening often while compressing a spring before the two parts can be assembled. The tiny needles are produced in the form of coil tubing and vary significantly from straightness after they are cut to length. This leads to difficult assembly problems if the needle must be passed through a small opening. The extremely sharp tip will catch the edge of a hole and jam the production line.

The rare prior art that employs a front mounted retraction mechanism in a one-piece barrel with a plugged hollow plunger, Tsao U.S. Pat. No. 5,084,018, among other things does not show reduced barrel area to prevent excessive blowout pressure, employs engaging flanges to secure all retraction parts, requires concurrent distortion of internal parts and flanges to effect release, cumulating in excessive force required to retract and requires ventilation holes because of a compartmented barrel.

The prior art has not produced a retractable nonreusable tamperproof syringe for mass production and assembly which is simple, reliable, cost effective, easy to use and retract, looks like a conventional syringe, has few parts which are easy to make and assemble, is not temperature sensitive and not subject to danger of premature retraction.

The prior art has not recognized a retraction mechanism with separable parts that relies entirely on clamping force or friction at a smooth walled reduced diameter transition zone in the barrel with mating lands which are slidably or separably released in response to relatively low thumb pressure while having resistance to premature retraction and high blowout pressure resulting from high pressure produced in the fluid chamber during an injection. The prior art has not recognized that such a structure can be molded as a one piece outer body over a core that can be pulled out from behind allowing the retraction mechanism to be easily pushed into place from behind, steered by the narrow nose portion. Neither does the prior art in such a combination realize the desirable non-cumulation of forces resisting retraction in order to minimize the thumb force required, having a most simple tamperproof feature and the fewest number of easily made parts.

The syringe plunger assembly has a combination of features not found in a prior art syringe. A head end which acts like a piston when installed in a syringe barrel has a reduced diameter front end having an opening and a dislodgeable stopper slidingly mounted in the opening projecting forwardly from the tip. Cooperating lands within the opening and on the head of the dislodgeable stopper seal the opening into the hollow interior of the plunger. The area of the stopper is relatively small when compared to the area exposed to the piston, which compresses fluid in a chamber below the piston. The ratio of the total area of the fluid chamber to the fluid exposed area of the stopper is at least two to one, more preferably three to one or more so that the stopper requires less holding force without blowing out back into the internal cavity. The cooperating lands have sufficient length so that the stopper can move back to the tip when the plunger moves forward at the end of an injection stroke without unsealing the plunger opening. A reduced holding force is sufficient to prevent blowout of the stopper after the stopper has been moved back to the tip because the stopper is exposed to a lower pressure generated force because of its relatively smaller area. The back of the plunger is vented so that entry of retractable parts which upon retraction finish dislodging the stopper and carry it back into the cavity, do not generate internal pressure that can blow out the nose of the syringe carrying any residual fluid with it. The thumb cap on the plunger is received and recessed into the opening at the back of the barrel when retraction occurs. The plunger cannot be grasped after this occurs to help prevent reuse.

These features and more are found in the inventive combination herein further disclosed which is especially suited for high speed production and assembly at low cost.

SUMMARY OF THE INVENTION

The invention is a reliable retractable tamperproof syringe having multiple tamperproof features which operates on a principle which permits low cost parts which are few in number and well suited for high speed mass production and assembly. The syringe structure features a one piece hollow outer body having a longitudinally extending wall which is stepped. The wall comprises an elongated barrel and nose with a transition zone connecting the barrel and nose. The nose has a reduced diameter relative to the barrel. The outer body has an inwardly facing surface in the wall at the most constricted part of the transition zone where the nose begins. A plunger assembly is disposed partially within the elongated barrel with an end cap for depression of the plunger extending from an opening in the back of the barrel. The head of the plunger, which has a retraction cavity for receiving parts of a retraction mechanism, moves in slidable sealed contact with the interior of the barrel.

A retraction mechanism is lodged in the nose of the body. The retraction mechanism comprises an elongated needle holder and spring combination wherein the needle holder has an elongated body with a needle holding portion in front and a head in back. The head of the needle holder has a cooperating outwardly facing surface configured to cooperate with said inwardly facing surface along an interface oriented in the direction of retraction to produce a holding force on the needle holder when installed in the nose in the unretracted position. The needle holder and spring are easily installable from the rear of the barrel toward the nose and releaseably held by sliding engagement of said cooperating inwardly and outwardly facing surfaces while compressing the spring and thereby producing a holding force on the needle holder in opposition to the retraction force applied to the needle holder by the spring. The parts are circular in cross section.

The outwardly facing surface on the circular head of the needle holder is slightly greater in diameter than the circular inward facing surface in the wall at the most constricted portion where the nose begins. The needle holder is thus clamped in position by hoop stresses induced in the outer body and held in position by frictional holding force. The needle holder is released in response to depression of the plunger to a retraction position. Retraction occurs in response to thumb force on the plunger when a portion of the plunger passing into the transition zone separates at least a portion of the inwardly and outwardly facing cooperating surfaces thereby reducing the holding force on the needle holder to an amount less than a retraction force on the needle holder produced by the spring whereby the needle holder is retracted into the cavity a distance sufficient to withdraw an injection needle, attached to the needle holder, into the outer body.

In one embodiment, the head of the needle holder is a two part head comprising an inner head surrounded by a separable retainer member wherein the outer surface of the retainer member is the outwardly facing surface with cooperates with the inwardly facing surface in the wall to retain the needle holder in an unretracted position at the most constricted part of the transition zone where the nose begins. The retainer member is a ring member coupled to the inner head along a sliding interface oriented in the direction of retraction with a friction force which exceeds the retraction force provided by the spring. The front of the needle holder is grounded in the nose portion against forward movement. The plunger head is configured to pass through the most constricted area and push against the retainer member without also pushing against the head of the needle holder. An alternate construction of the two part head of the needle holder comprises the separable retainer member being tack welded to the inner head of the needle holder, preferably along a very small ridge or bridge between the mating surfaces which holds the two part head together until the bridge is ruptured by movement of the plunger after an injection has occurred.

The front of the plunger has an opening for a stopper slidingly fitted therein in an interference fit. The stopper is fitted in the opening in an interference fit along a sliding interface oriented in the direction of retraction. The stopper is mostly or fully dislodged by contact with the retraction mechanism at the end of an injection cycle by continued depression of the plunger from a first position at the end of the injection cycle to a second position with the tip of the plunger in contact with the retainer ring. This avoids cumulation of the force on the plunger required to dislodge the stopper from the opening and the force required to dislodge the retainer member from the head of the needle holder and outer body wall. Upon further depression of the plunger from the second position to the retraction position, the frictional holding force on the needle holder is reduced until the retraction force provided by the spring exceeds the remaining holding force and the needle holder and needle connected thereto are ejected into the cavity carrying the dislodged stopper along with them. The dislodging of the stopper and the retainer member alone make the syringe non-reusable. The plunger cannot be removed after retraction because the graspable end cap enters an opening at the back of the barrel when the plunger is depressed to the retraction position to prevent tampering after retraction.

The retraction cavity of the plunger is preferably vented to prevent a puff of air coming forward at the instant of retraction from blowing a tiny amount of retained fluid from the nose. This condition can occur if the plunger is fully depressed to release the needle holder and dislodge the stopper while the needle is physically restrained from retracting by the septum of a vial which has just been filled with fluid from the syringe. The thumb cap at the rear of the syringe is preferably provided with channels in fluid communication with the interior in cooperation with a closure removably installed in a centrally located opening in the thumb cap. One or more stepped portions of the opening and closure provide seating for the closure. Undercut portions at the side of the closure together with grooves in the interior surface of the plunger wall create passages for air to vent through channels on the thumb cap. This structure prevents air from being trapped by the user's thumb when the thumb cap is pressed to fire the syringe. One or more slots at the back of the barrel around the opening which receives the thumb cap prevent vented air from being trapped by the user's thumb when the plunger is fully depressed.

The syringe has a high blowout pressure and a low plunger thumb force required to cause retraction. Blowout pressure is the fluid pressure operating on the stopper and retainer ring during an actual injection. High blowout pressure resistance is obtained because the retainer ring is mounted in the most constricted portion of the barrel where the nose begins which significantly reduces the amount of area exposed to fluid pressure. The smaller retainer ring allows the use of a small needle holder such that the opening in the plunger and the stopper can be only a fraction of the cross sectional area of the fluid chamber below the plunger head. The ratio of the greatest cross sectional area of the variable chamber and that of the dislodgeable stopper or the ring member are selected so that the maximum expected thumb force on the plunger during an injection will produce a maximum pressure in the chamber which will generate a blowout force on the stopper and retainer member slightly less than the amount of dislodging force necessary to dislodge the stopper and retainer member during retraction. This ratio should be at least two to one, or more preferably three to one or more, in order to ensure against premature blowout of the stopper or retainer ring.

In an alternate embodiment, the fewest number of easily made separate parts are used in a retractable syringe. The alternate embodiment has a similar stopper in the head of the plunger and a similar needle holder and spring combination with mating cooperating inwardly facing and outwardly facing interengaged surfaces at the most constricted part of a transition zone where the nose begins. In the alternate embodiment, there is no retainer ring around the head of the needle holder. Instead a tiny ramp is provided at the transition zone or adjacent the transition zone whereby the head of the plunger gently spreads the barrel outwardly while dislodging the stopper thereby reducing the clamping or friction force on the head of the needle holder provided by the wall of the outer body. The holding force is thereby reduced below the retraction force provided by the compressed spring and the needle holder is ejected into the cavity of the plunger carrying the dislodged stopper along with it.

Manufacture and assembly is facilitated by the fact that the plunger and the outer body can be molded with a non-collapsible core tool that can be pulled out from behind. The parts are simply shaped and do not have hooks and parts with reentrant angles that require collapsible core pin technology. The outer body can be made in one piece and assembled from the rear. The narrowed nose portion provides no lateral space with will permit bunching of the spring and jamming when the retraction assembly is moved forward in the outer body. In fact, the nose serves as a guide to steer the parts into the proper position in one smooth stroke.

The needle does not have to be installed before the retraction mechanism is put in place because it is readily installed from the front after the needle holder is slidingly lodged in the nose. Significant variations in the holding force on the needle holder and the dislodging force on the stopper due to slight variances in the tolerance of the mating parts is avoided because the longitudinal wall of the outer body has some flexibility. The wall can spread outwardly slightly and the stopper and head of the needle holder can compress slightly radially and expand slightly in the longitudinal direction to avoid significant changes in the holding force caused by small changes in the actual diameters. Consistency in the amount of retraction force is thereby provided and economy is assured.

DETAILED DESCRIPTION OF THE PREFERRED EMBODIMENT

Figures 1, 2:
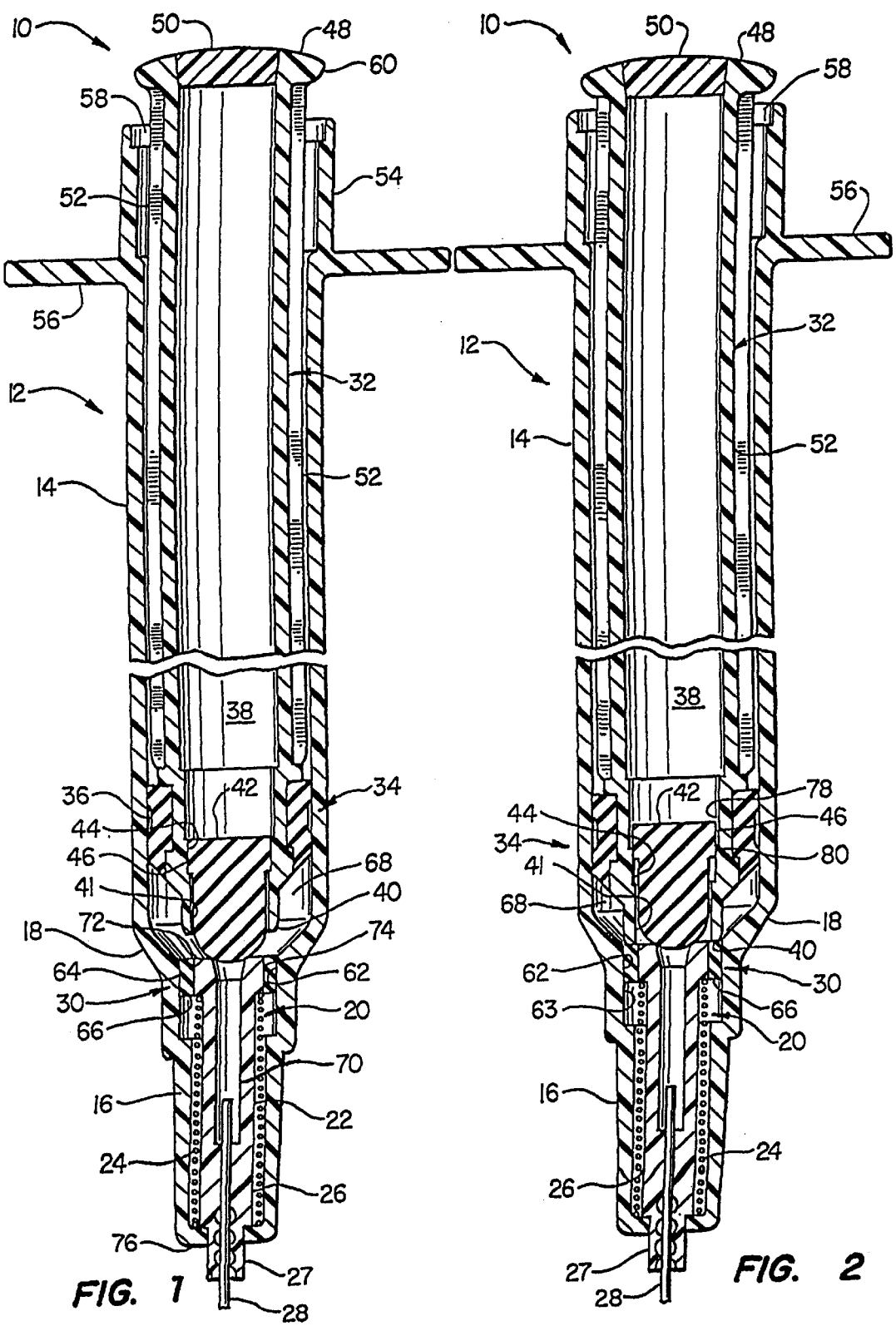
FIG. 1 is a cross section along the central axis of a first embodiment of the invention with the plunger positioned in a first position at the end of an injection cycle.
FIG. 2 is the syringe of FIG. 1 with the plunger depressed additionally to dislodge the stopper at a second position of the plunger wherein the tip of the plunger is ready to operate the retraction mechanism.

In the description that follows, like parts will be referred to by the same reference numerals. Parts with a subscript letter are mean to illustrate a minor variation of a part with the same number. The drawings are enlarged significantly in order to show the details of the invention but generally reflect the true scale which is contemplated. The parts as shown are understood to be preferably circular and symmetrical as is conventional for syringes. The drawings reflect a syringe structure typically having a 1 cc to 3 cc injection fluid capacity.

FIG. 1 shows the structure of the first embodiment generally referred to by reference numeral 10. Syringe 10 has a one piece hollow outer body 12. Body 12 has a longitudinally extending wall comprising an elongated barrel 14 and a nose 16 with a transition zone 18 connecting the barrel and nose. A front mounted retraction mechanism lodged in the nose is generally referred to by the reference numeral 20. It comprises the combination of an elongated needle holder 22 and spring 24. The needle holder has an elongated body with a needle holding portion 26 in front for holding a needle 28 and a head 30 in back. Head 30 may consist of a two part head as in FIGS. 1–3 or a one part head as in FIGS. 5–7. The needle holder is released by depression of a plunger that win be described.

A plunger generally designated by the reference numeral 32 is disposed for use partially within barrel 14. The plunger has a head and seal generally referred to by reference numeral 34, in slidable sealed contact with the interior of barrel 14 of outer body 12. The plunger has a seal element 36 that is conventional and a retraction cavity 38 therein.

Head 34 has a tip portion 40 forming an opening 41 into retraction cavity 38. A resilient dislodgable stopper 42 is sealingly positioned in opening 41 with a front portion thereof extending beyond tip 40. Head portion 34 and the back part of stopper 42 have cooperating lands 44, 46, respectively, which seal opening 41. Plunger 32 has an end cap 48 for depression of the plunger by the thumb. End cap 48 has a central opening for permanently receiving force fit plug 50 to close retraction cavity 38 at the back end.

Figure 4A:
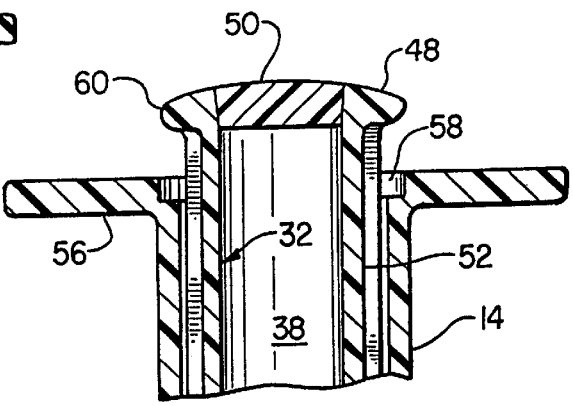
FIG. 4A is a partial cross section on the central axis of an alternate tamperproof opening in the back of the outer body prior to retraction.
Figure 4B:
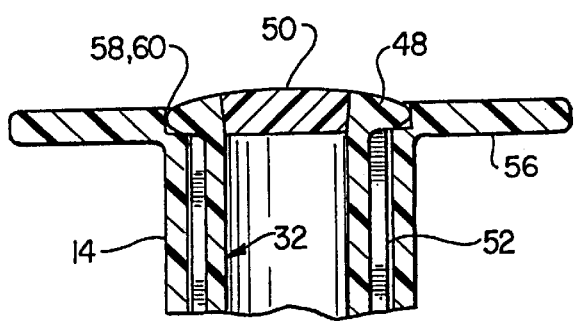
FIG. 4B is the structure of FIG. 4A with the plunger in the retracted position received in an opening at the back of the outer body.

A plurality of longitudinally extending flutes 52 slidingly support plunger 32 in barrel 14. In the embodiment of FIG. 1, outer body 12 has a collar 54 extending behind finger grips 56 having opening 58 which closely receives the outer periphery 60 of cap 48 when the plunger is depressed to the retracted position. An alternate arrangement is shown in FIGS. 4A and 4B in which barrel 14 is extended longitudinally, if necessary, so that end cap 48 fits closely within an opening at the back of the barrel where the finger grips are. FIG. 4B shows the tamperproof position with the plunger in the retracted position. It should be noted that depending on the relationship of the inside diameter of the barrel and the diameter of the end cap, the end cap could instead be received right inside the opening at the back of the barrel. Regardless of how the end cap in back of the outer body and barrel are configured, the plunger can no longer be grasped after retraction has occurred because end cap 48 is depressed into an opening.

The wall of outer body 12 and head 30 of the needle holder have mating cooperating smooth surfaces which hold needle holder 22 in the position shown in FIG. 1 with spring 24 compressed. Nose 16 has a reduced diameter relative to the barrel. The outer body has a most constricted part where head 30 of needle holder 22 is engaged and held. The outer body has an inwardly facing surface 62 at the most constricted part of the transition zone where nose 16 begins. Similarly, head 30 has an outwardly facing surface 64 configured to cooperate with inwardly facing surface 62 to produce a holding force on needle holder 22 when the retraction mechanism is installed in the nose from the rear. Mating surfaces 62, 64 constitute a sliding interface oriented in the direction of retraction, which seals nose 16. Mating surfaces 62, 64 are preferably friction surfaces which have an interference sliding fit to apply a frictional holding force which holds needle holder 22 in position by friction between the mating parts. It is within contemplation of the invention that one or more of the cooperating interface surfaces could employ a coating or adhesive bond which is ruptured or released when the mating surfaces or lands are separated or moved relative to each other.

Head 30 provides a lower boundary for a variable fluid chamber 68 below head 34. Needle holder 22 has a fluid path 70 in fluid communication with fluid chamber 68 and needle 28. Needle holder 22 has a smaller diameter inner head 72 which is part of head 30. Retainer member 66 is coupled to inner head 72 along sliding interface 74 oriented in the direction of retraction. Retainer member 66 is coupled to inner head 72 with a holding force which exceeds a retraction force applied to the underside of inner head 72 by means of the end of compressed spring 24. A reduced diameter portion 27 of needle holder 22 protrudes through an opening in front 76 of nose 16.

Importantly, retainer member 66 can be visualized as an annular ring surrounding circular inner head 72. The location of retainer member 66 at the most constricted part of the transition zone where the nose begins and the relatively small area exposed to pressurized fluid in chamber 68 results in a high blowout pressure. Since the front portion 26 of the needle holder is grounded or bottomed inside front 76 of nose 16, no amount of pressure will allow needle holder 22 or needle 28 to move forward. Blowout pressure may be defined as the pressure in chamber 68 acting on the exposed area of retainer member 66 to produce a force sufficient to overcome the holding force such that retainer 66 could "blowout" by moving forward and prematurely release needle holder 22.

Some users have strong hands and might, at the outer limit in an emergency, be able to generate a force of as much as fifteen to eighteen pounds on the plunger during an injection. It is considered almost impossible for anyone to exert a force of more than eighteen pounds. This may be regarded as the maximum expected force which must be taken into account so that ring member 66 will not blowout while an injection is being made. The greatest cross sectional area of variable chamber 68 and the area of retainer member 66 exposed to fluid pressure are selected so that the blowout pressure is higher than the maximum pressure in chamber 68 expected to result from the maximum expected thumb force applied to cap 48 during an injection. This ratio is preferably about two to one and more preferably about three to one or more so that the holding force holding the retraction mechanism in place can be kept at a comfortably low level while the blowout pressure remains high.

Dislodgeable stopper 42 has a similar blowout problem to recognize. The front and middle portion of stopper 42 are relieved slightly from opening 41 such that the fluid pressure in chamber 68 is directed against the cross sectional area at cooperating lands 44, 46 and could cause stopper 42 to blowout. A frictional holding force is generated at the lands 44, 46 which may be called a dislodging force which must be overcome to slide stopper 42 rearwardly before retraction. The ratio of the maximum cross sectional area across the interior of variable chamber 68 to the maximum cross sectional area of stopper 42 exposed to pressure in chamber 68 are selected so that the maximum expected thumb force on plunger 32 during an injection will produce a maximum force slightly less than the amount of dislodging force necessary to dislodge the stopper so that stopper 42 will not blowout during an injection. This ratio is preferably not less than about two to one, more preferably three to one or more, whereby a force of about eighteen pounds on the plunger, for example, would produce a pressure generated force of only about nine or six pounds, respectively, on the stopper, so that the stopper can be easily dislodged in advance of retraction at the end of the injection cycle but will not blowout during an injection. The stopper is dislodged after the injection by thumb force applied to the stopper by movement of the plunger.

The components used for retraction are arranged to avoid cumulation of force during the retraction sequence. In FIG. 1, stopper 42 has a forward extension beyond tip 40 which allows full thumb pressure to be applied to the stopper before any other portion of the retraction mechanism is engaged. The amount of forward extension beyond tip 40 is related to the length of lands 44, 46 such that the forward extension of stopper 42 preferably represents about 80 percent of the engaged land length. When stopper 42 is moved back until the front is even with tip 40, as seen in FIG. 2, only about 20 percent of engaged land remains. In FIG. 2 it can be seen that thumb force on plunger cap 48 has been applied to partially dislodge stopper 42 such that a gap 78 is created and the remaining engaged land area is represented as area 80.

Since I believe the amount of frictional holding force or dislodging force is roughly proportional to the amount of the length of the sliding interface between cooperating lands 44, 46, it follows, ignoring dynamic effects, that the amount of force remaining decreases as the engaged sliding interface area is reduced. This is what happens as stopper 42 moves back into cavity 38 from the position of FIG. 1 to the position of FIG. 2. It is believed appropriate to set the initial dislodging force to allow about five pounds at the position of FIG. 1 which is reduced to about one pound remaining when the stopper or plug member 42 reaches the position of FIG. 2. It might be noted at this point in the description that the front portion of tip 40 preferably has some longitudinally extending slits or openings so that fluid is not trapped in the trapezoidal shaped area of chamber 68, seen in FIG. 2, because of contact between tip 40 and the upper surface of retainer ring 66.

Needle holder 22 and spring 24 are combinably installable from the rear of the barrel before the plunger is assembled and releasably held at the most constricted part of the transition zone where the nose begins by sliding engagement of the cooperating inwardly and outwardly facing friction surfaces 62, 64 while compressing spring 24. The length of the engaging land 64 and the amount of interference fit is preferably designed to provide a frictional holding force in opposition to the retraction force provided by the compressed spring 24 of somewhere around five pounds even though the spring may apply a retraction force in the retraction direction of somewhere around a half pound. In use the needle is pushed against a rubber seal in a vial so the needle holder must resist a resulting backward force without being dislodged during the filling operation. This requirement and blowout pressure limits the low end of the holding force on the needle holder.

Figure 3:
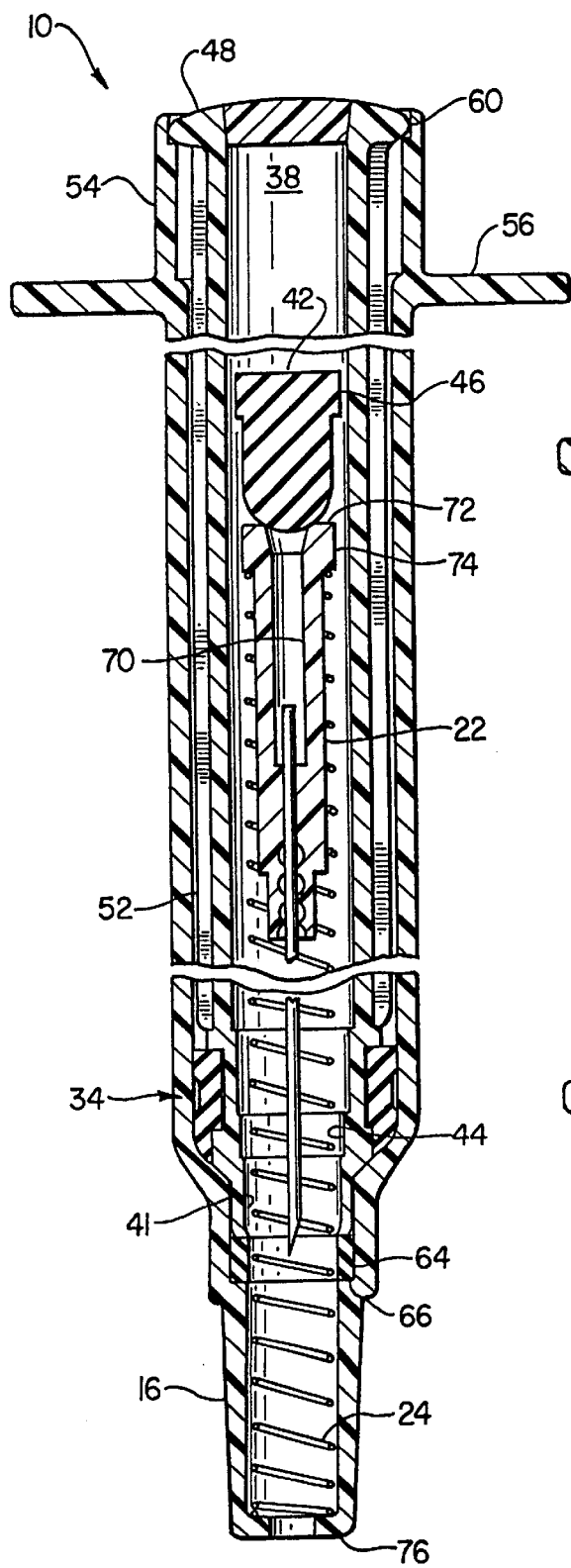
FIG. 3 is the syringe of FIG. 2 wherein the plunger has been further depressed to a retraction position, retraction has occurred and the cap at the back of the plunger is closely received in an opening at the back of the outer body.

Referring again to FIG. 2, it can be seen that further depression of the plunger beyond the second position of FIG. 2 dislodges retainer ring member 66 along the sliding interface 74 provided by the outer surface of inner head 72 and along the inwardly facing friction surface 62. As the amount of remaining engaged interface is reduced, the amount of force required to continue moving retainer member 66 off needle holder 22 is reduced and the small remaining engagement area 80 between lands 44, 46 of the plunger and stopper preferably cause stopper 42 to be dislodged before needle holder 22 is released. When the remaining residual friction force during continued depression of the plunger becomes less than the retraction force provided by compressed spring 24, the retraction position of FIG. 3 is reached whereby retraction occurs.

When retraction occurs needle holder 22 moves through opening 41 into cavity 38. The uncompressed length of spring 24 is selected to provide backward movement sufficient to withdraw an injection needle 28 fixed in front portion 26 entirely within outer body 12, carrying dislodged stopper 42 with it. At the same time, cap 48 enters opening 58 of the barrel with peripheral edge 60 closely confined, in order to prevent tampering after retraction. It is immaterial whether cap 48 moves into the opening at the instant of retraction or after retraction has already occurred because the movement is automatic due to the continued thumb force applied to trigger the retraction. Sufficient unengaged length of inwardly facing friction surface 62 is provided so that retainer member 66 can move downwardly a sufficient distance to reach the retraction position of FIG. 3. After retraction, retainer member 66 preferably remains stuck and prevents any possibility of any one being able to reengage it with the head of needle holder 22. The diameter of land 62 in the area designated 63 can be increased slightly to provide relief for retainer ring 66 as it is pushed down by tip 40.

Figure 8:
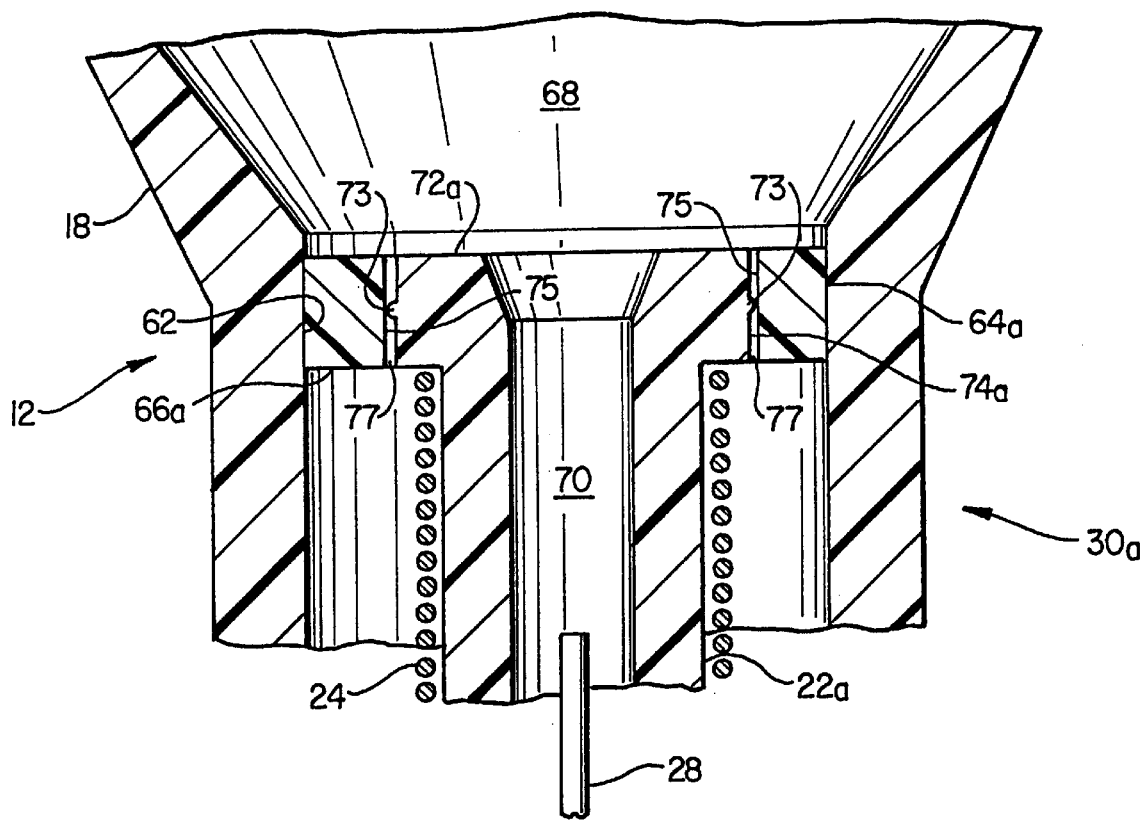
FIG. 8 is a schematic longitudinal cutaway view in elevation through the center of the two part head showing how a tack weld can be applied to simultaneously seal and hold the retainer ring in place on the needle holder.

It is also within the contemplation of the invention that separable retainer member 66 may be removably coupled to inner head 72 of needle holder 22 by means of a relatively small in area "tack" weld which is sufficient to resist the retraction force applied to needle holder by spring 24 but which can be ruptured or separated by depression of the plunger beyond the position shown in FIG. 2, to release the needle holder and allow retraction. This is schematically illustrated in FIG. 8 with respect to alternate head 30*a* with the parts of syringe body 12 and needle holder 22 cutaway to focus on the modification. The remainder of the syringe structure would be like FIGS. 1–3.

In FIG. 8, inner head 72*a* has an outwardly facing surface 74*a* and a very small raised portion or series of horizontally spaced apart raised portions 73 around the periphery in a continuous band or annular ring which extend relatively uniformly outwardly beyond peripheral surface 74*a* of head 72*a*. The raised portion could be on the inner surface 75 of retainer 66*a* instead of being on surface 74*a* of the needle holder. The head of the needle holder is preferably circular but could be conceivably another shape with the retainer member 66*a* correspondingly configured to conform to it.

The inwardly facing surface 75 of inner head 72*a* is in contact with raised portion 73 on the outer surface of inner head 72*a* and there may be a small gap 77 between them all around. The raised portion 73 couples retainer 66*a* to inner head 72*a* and may be referred to as a bridging portion which resists the blowout pressure referred to above and holds the needle holder in place against the retraction force imposed on the needle holder by spring 24 together with any small additional forces that may be applied when the needle is pushed against the rubber seal of a vial in preparation for use. The bridging portion may be formed by "tack" welding the raised portion 73 to the inner surface of the ring 66*a* or by providing any other form of frangible bridging portion that holds the separable ring member 66 and needle holder head 72*a* together. It is required that however done, the bridging portion must also serve as a seal between the facing surfaces of the ring member and inner head so that fluid under pressure cannot pass from chamber 68 through gap 77 to reach the nose portion of the device. All fluid must pass through fluid passage 70.

It can be seen that when the position of FIG. 2 is reached the front tip 40 of the plunger presses against retainer ring 66*a* after stopper 42 is almost dislodged and uncouples the retainer ring 66*a* from the inner head 72*a* of needle holder 22*a*. Any tack weld connecting the separable parts at the bridging portion is ruptured, fractured or otherwise separated so as to separate retainer ring 66 a from inner head 72*a* thus releasing needle holder 22*a* from further restraint. They and the force applied by spring 24 causes retraction to occur much as before described and shown in FIG. 3.

It is believed that the increased diameter of the raised portion 73 should be within the range of about 1 to 8 thousandths of an inch which may be dictated by the ability of the molding equipment available to produce a consistent bridging portion without defects. It is believed that it may be desirable to employ different polymeric materials for the retainer ring and needle holder to facilitate tack welding, such as a suitable polyvinyl chloride (PVC) for the retainer ring and a suitable polycarbonate plastic material for the needle holder. One way to couple these two parts may be to assemble them and expose them to a temperature of about 120° C. for twenty minutes or so to allow some diffusion or incipient melting to occur where they touch. The raised portion creates a high unit pressure where it comes into contact with the inwardly facing surface of retainer 66a. Sonic welding could also be employed. A coating or adhesive which couples the retainer ring to the needle holder and can be uncoupled by means of force applied to the retainer ring by the plunger is also within the contemplation of the invention.

Figures 5, 6:
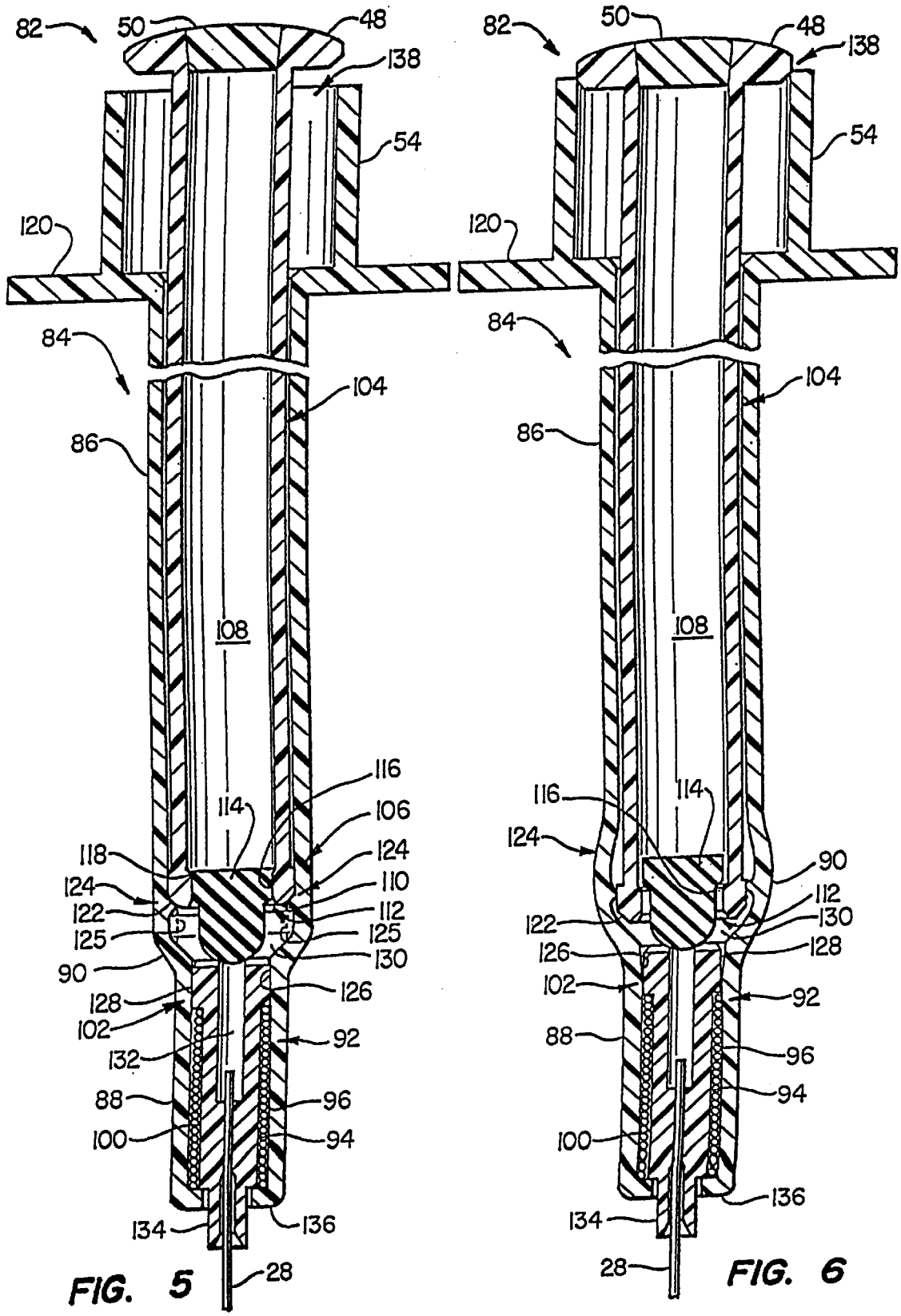
FIG. 5 is a cross section along the central axis of a simplified alternate syringe structure without a retainer member around the needle holder, which is released by separation of the friction surfaces, shown in the plunger position which represents the end of an injection cycle.
FIG. 6 is the syringe structure of FIG. 5 wherein the plunger is further depressed to dislodge the stopper and begin to release the friction surfaces just prior to retraction.
Figure 7:
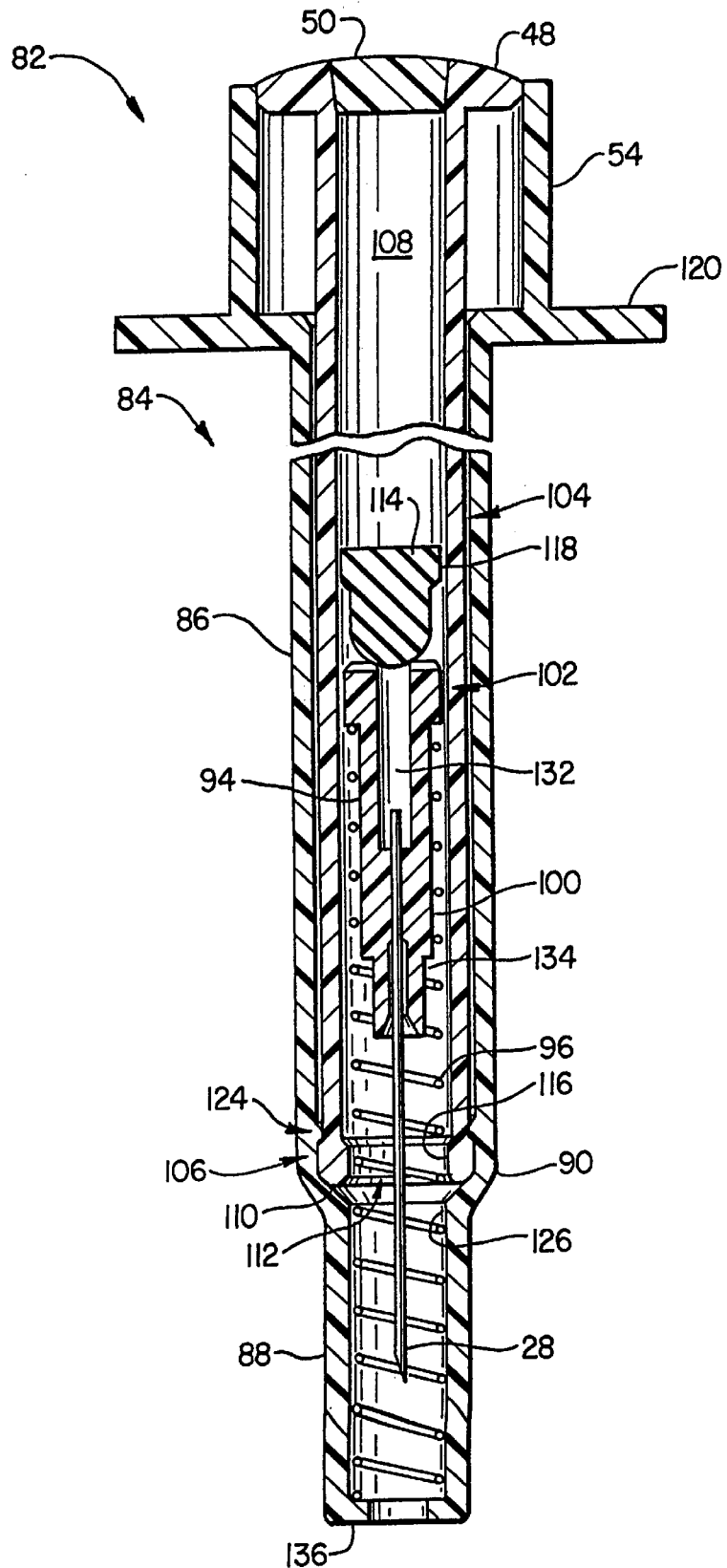
FIG. 7 is the syringe structure of FIG. 6 with the plunger further depressed beyond the position of FIG. 6 to the retraction position where retraction has occurred and the cap is secure within an opening in the back of the hollow outer body.

An alternate syringe 82 is disclosed in FIGS. 5–7. In FIG. 5, Syringe 82 has a one piece hollow outer syringe body 84. Body 84 has a longitudinally extending wall comprising an elongated barrel 86 and a nose 88 with a transition zone 90 connecting the barrel and nose. A front mounted retraction mechanism lodged in nose 88 is generally referred to by the reference numeral 92. It comprises the combination of an elongated needle holder 94 and spring 96. The needle holder has an elongated stem body with a needle holding portion 100 in front for holding needle 28 and a head 102 in back. In this case, head 102 is a one part head integral with the rest of needle holder 94. Spring 96 delivers a retraction force in a retraction direction to the underside of head 102.

A plunger generally designated by reference numeral 104 is disposed for use partially within barrel 86. Plunger 104 has a head portion 106 which moves in slidable sealed contact with the interior of barrel 86 of outer body 84. Although a separate seal might be used on head 106, this embodiment is suitable for a smaller diameter, such as a 1 cc syringe, and can be used with head 106 also serving as the seal. A retraction cavity 108 is provided in the interior of hollow plunger 104. Head 106 has a tip portion 110 forming an opening 112 for a dislodgable stopper 114 having a front portion extending beyond tip 110. Head portion 106 has an inwardly facing land 116 and the back of stopper 114 has an outwardly facing land 118 comprising cooperating friction surfaces which seal opening 112. The back portion of outer body 84 may have finger grips 120 and the same collar 54 and end cap 48 previously disclosed. The alternate arrangement of FIGS. 4A and 4B may also be employed.

The outer portion of tip 110 may be equipped with an angled surface 122 designed to cooperate with a small ramp surface 124 located in the vicinity of transition zone 90. The wall of outer body 84 and head 102 of the needle holder have mating cooperating friction surfaces which frictionally hold needle holder 102 in the position shown in FIG. 5 with spring 96 compressed. Nose 88 has a reduced diameter relative to barrel 86. The outer body has a most constricted part where the head 102 of needle holder 94 is frictionally engaged. The outer body has an inwardly facing surface or land 126 at the most constricted part of the transition zone where nose 88 begins. Similarly, head 102 has an outwardly facing friction surface 128 configured to cooperate with inwardly facing surface 126 to produce a frictional holding force on needle holder 94 when the retraction mechanism is installed in the nose from the rear.

Mating surfaces 126, 128 constitute a sliding interface oriented in the direction of retraction, which seal nose 88. Mating surfaces 126, 128 are preferably smooth friction surfaces which have an interference sliding fit when needle holder 94 is installed from the rear whereby a frictional holding force holds needle holder 94 in position by friction between land 126 and head 102 of needle holder 94. It is within contemplation of the invention that one or both of these surfaces could have a coating or adhesive bond which is ruptured when the mating surfaces are separated to release the needle holder.

Head 106 provides the upper boundary for a variable fluid chamber 130 below head 106. Needle holder 94 has a fluid path 132 in fluid communication with chamber 130 and needle 28. Needle holder 94 is releasably coupled at surfaces or lands 126, 128 with a holding force that exceed the retraction force applied to the underside of head 102 by the end of compressed spring 96. A reduced diameter portion 134 of needle holder 94 protrudes through an opening in front 136 of nose 88. Blowout pressure is not a factor with respect to the needle holder on the alternate embodiment. No amount of pressure will allow needle holder 94 or needle 28 to move forward since the front portion 100 of the needle holder is grounded or bottomed inside front 136 of nose 88.

Blowout pressure is still a factor to be considered in connection with stopper 114. Blowout pressure would be the pressure in chamber 130 produced by thumb force on cap 48 acting on the cross sectional area of stopper 114 which could overcome the holding force, causing stopper 114 to dislodge from opening 112 prematurely. The ratio of the maximum cross sectional area across the interior of variable chamber 130 to the maximum cross sectional area of stopper 142 exposed to pressure in chamber 130, and the dislodging force necessary to dislodge stopper 144, are selected so that the maximum expected thumb force on plunger 104 during an injection will not cause the stopper to blowout. Yet the stopper will still be dislodged by the dislodging force on the plunger once the front of stopper 114 contacts the retraction mechanism after the injection has ended. The ratio referred to is preferably not less than about two to one, or more preferably about three to one or more, whereby a force of about eighteen pounds on the plunger, for example, would produce a pressure generated force of only about nine or six pounds respectively, on the stopper, so that the stopper can be easily dislodged in advance of retraction at the end of the injection cycle but will not blowout during an injection. The smaller diameter stopper allows two or three times the thumb force to be used during the injection cycle than required to actually dislodge the stopper by direct application of force.

By reference to FIGS. 5–7, the operation and further features of the alternate embodiment are discussed. The syringe is used in the normal manner until the plunger is depressed to the first position of FIG. 5 which is the end of the injection cycle. Stopper 114 has a forwardly extending end which has come into contact with head 102 of needle holder 94 to block fluid path 132. Further depression of plunger 104 toward the position of FIG. 6 mostly or filly dislodges stopper 114 and begins spreading barrel 84 at the transition zone by sliding contact between head portion 106 and ramp 124. Ramp 124 is a very small inwardly extending annular thickening of the wall of barrel 86 which can take many shapes or forms. For example, ramp 124 may be a small step 125 in the wall which continues vertically downward as indicated by the dotted line, which is somewhat exaggerated in FIG. 5.

The barrel is flexible and is spread outwardly a slight amount to the position of FIG. 6 just prior to retraction. Here the mating surfaces 126, 128 are separated an amount which reduces the clamping force on the needle holder 94. The spreading shown in FIG. 6 is greatly exaggerated for illustration. It is estimated that an expansion of only about four thousandths of an inch is sufficient to release needle holder 94 from nose 88. By slight further depression of the plunger from the position of FIG. 6 to the retracted position of FIG. 7, retraction occurs when the retraction force applied by spring 96 exceeds the remaining holding force on needle holder 94. Needle holder 94 then moves through opening 112 into cavity 108 along with a portion of spring 96. The uncompressed length of spring 96 is designed to provide sufficient backward movement to withdraw an injection needle 28 fixed in front portion 94 and carry dislodged stopper 114 with it. At the same time, cap 42 enters opening 138 at the rear of a barrel extension 54 where the peripheral edge is closely confined in order to prevent tampering after retraction.

The location and configuration of ramp 124 is arranged to avoid cumulation of force required during the retraction sequence. Most of stopper 114 should be dislodged by thumb pressure on plunger 104 before significant resistance develops as angled surfaces 122 begin pushing outwardly on ramp 124. The selection of the location of ramp 24 and the angle of the engaging surfaces make it possible to have a fairly smooth continuous force since the dislodging force continuously decreases as the sliding interface area 116, 118 between the plunger and the stopper is linearly decreased. Because ramp 124 is relatively very small, it is still possible to remove a stepped molding core from the rear of the outer body 84. Alternately, ramp 124 can be the smaller diameter step 125 which avoids reentrant angles whereby resistance to removal of the molding core could occur. After retraction, the back of the plunger is unaccessible and there is no way to reach to stopper or the needle holder in order to reinstall them for re-use.

When used normally, syringe 10 may have a small amount of fluid remaining in the variable chamber in the second position shown in FIG. 2 which is, of course, greatly exaggerated in scale. This may amount to no more than a drop or a few drops of fluid in the remaining space above the retraction mechanism. When syringe 10 is fired by pushing down on end cap 48, to the position of FIG. 3, the expanding spring and rearwardly moving needle holder carry any remaining fluid up into retraction cavity 38. Surface tension effects hold the tiny droplets in place along the walls of the plunger and no fluid escapes from nose 16. The syringe is normally used to withdraw fluid from a vial. The fluid is injected into a patient followed by immediate retraction of the needle holder and needle in one step. No leakage of fluid from the nose is observed when the syringe is used to inject fluid into a patient.

It has been discovered, however, that if the needle is forcibly prevented from retracting after syringe 10 is "fired" by pushing down until plunger 48 enters opening 58, the small amount of retained fluid from variable chamber 68 can flow into the nose in the space between the needle holder and nose. If the seal around the head of the needle holder is removed while the needle holder is being restrained from retracting, remaining fluid has time to move down into the nose, but it does not leak out from the opening in the front of the nose. Then if the needle holder is suddenly released and allowed to retract normally, it has been found that leakage of fluid from the opening in the front of the nose could be observed. This undesirable scenario was found to occur under the following circumstances. If the syringe is used to draw blood from the patient, the blood filled syringe is removed from the patient and the needle passed through a rubber septum in a sterile vial. The plunger is then depressed to discharge the patient's blood into the vial. Users expect to depress the plunger fully after the fluid is discharged to retract the needle. When the plunger is depressed fully to cause retraction, the needle cannot retract normally due to the fact it is frictionally held by the rubber septum of the vial. When the empty syringe is then withdrawn from the vial by pulling the needle out of the septum, it immediately retracts. Droplets of fluid were observed on the vial as soon as retraction took place.

Surprisingly, it was found that a small "puff" of air is the source of this problem. If the needle or needle holder is temporarily restrained and prevented from retracting in the normal manner, a brief puff of forwardly directed air is generated when the needle holder is finally allowed to retract. This puff of air was found to emerge from the front of the syringe causing retained fluid trapped around the needle holder to be blown out of the opening left in the nose when the needle holder retracts. It was discovered that if the hollow interior of the plunger is vented, preferably in the area of thumb cap, this condition does not occur and the fluid is entirely retained within the syringe body.

FIGS. 9 through 16 illustrate the syringe generally designated as syringe 10 with a modification on the end cap or thumb cap on the plunger to provide for venting of the hollow interior of the plunger which is the retraction cavity. Insofar as possible the original numbering of FIGS. 1–4 is retained with primes used to indicate differences.

Head 34' of plunger 32' is preferably slightly modified from plunger head 34 of FIG. 2 in the following respects. The elongated plunger has a longitudinally extending generally tubular wall 140 defining a hollow interior along the length of the plunger. The plunger has a head end 34' in front and a rear end portion 142 with a thumb cap 48' behind. The outer side of wall 140 at head end 34' is sealingly surrounded with a resilient plunger seal member 36' which is like a band with a pair of separated raised rings 144. Plunger seal 36' fits in a depression in the outer surface of wall 140 where it is securely held in position and prevented from longitudinal movement. Seal member 36' is adapted to slide in sealed contact with a tubular wall when the plunger is moved within syringe barrel 14. It is within contemplation of the invention to have a raised piston molded as part of the plastic plunger to serve as a plunger seal in place of a separate rubber plunger seal 36', although the rubber seal member is preferred.

Wall 140 at head end 34' of the plunger 32' has a reduced diameter front portion extending forward from seal member 36' terminating at tip 40 at the front of plunger 32'. Tip 40 defines the opening 41 which leads into the hollow interior 38. The internal structure is as shown in FIG. 1. The wall 140 behind tip 40 has a stepped inner side surface comprising a land having an inwardly facing surface and a larger diameter portion extending behind the land into the hollow interior. A separate dislodgeable stopper 42 is slidingly held within the reduced diameter front portion of plunger head 34' by a holding force in excess of the fluid injection pressure force to be expected during use of the plunger in syringe barrel 14. Stopper 42 has a back end portion comprising a land 46 and a reduced diameter front end portion extending forwardly beyond tip 40 a fixed distance to its front 146. The fixed distance is the distance between front 146 and tip 40.

As is seen in FIG. 1, the outwardly facing surface 46 of dislodgeable stopper 42 is in sliding sealed engagement with the inwardly facing surface of land 44 in the plunger wall. These lands cooperate to apply a holding force to the stopper and seal hollow interior 38 of plunger 32' from the expected amount of fluid injection pressure force generated in the variable chamber 68 during an injection. The ratio of the effective area of variable chamber 68 to the area of stopper 42 exposed to fluid pressure is at least two to one and preferably three to one or more as previously indicated. This makes it possible to utilize lower holding forces without blowing out the stopper during an injection. The cooperating lands on the inside of the plunger head and the stopper have sufficient longitudinal length to allow dislodgeable stopper 42 to move the fixed distance between its initial extension at 146 and tip 40 in sliding response to forward movement of the plunger after front 146 of stopper 42 contacts a stop.

As indicated in FIGS. 1–3, front 146 of the stopper 42 encounters head 72 of needle holder 22 which serves as a stop. The fluid opening in head 72 of needle holder 22 is preferably provided with some fine slots or grooves so that fluid can continually enter fluid path 70 as the plunger moves from the position of FIG. 1 to that of FIG. 2. As the position of FIG. 2 is reached, the holding force on stopper 42 is reduced by substantial disengagement of the cooperating lands 44, 46 in preparation for dislodgement of the stopper, without unsealing the hollow interior/retraction chamber 38 within plunger 32'. A notch 148 is preferably provided in the tip to prevent trapping fluid at the tip.

Thumb cap 48' at the rear end portion 142 of plunger 32' includes one or more channels 150 which receive vented air from hollow interior 38. Thumb cap 48' has an opening 152 for a closure 154 best seen in FIGS. 10 and 11. Channels 150 are open at the top for ease of molding although closed channels could also be used.

Figure 10:
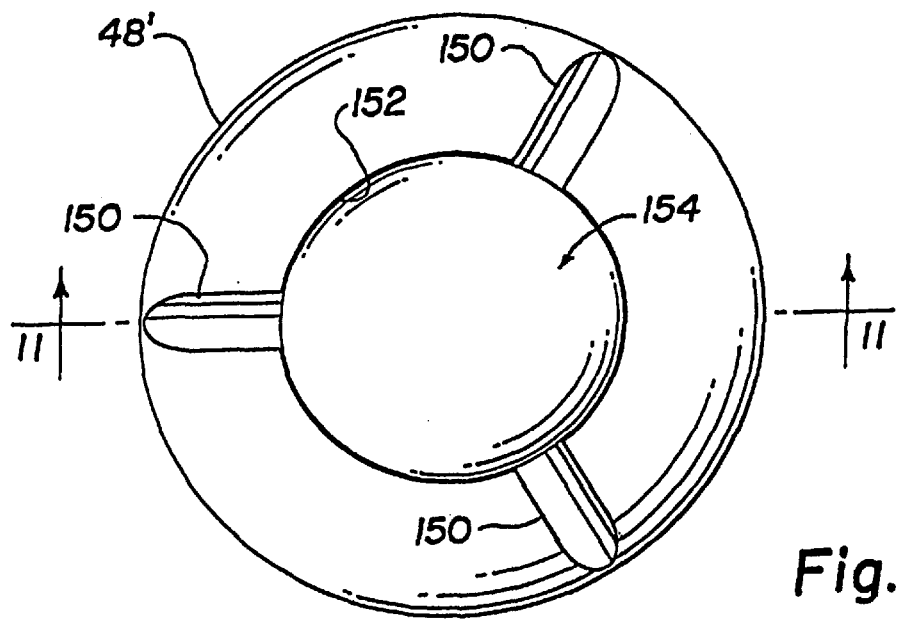
FIG. 10 is a plan view of the thumb cap of the plunger assembly shown in FIG. 9 with the preferred closure.
Figure 11:
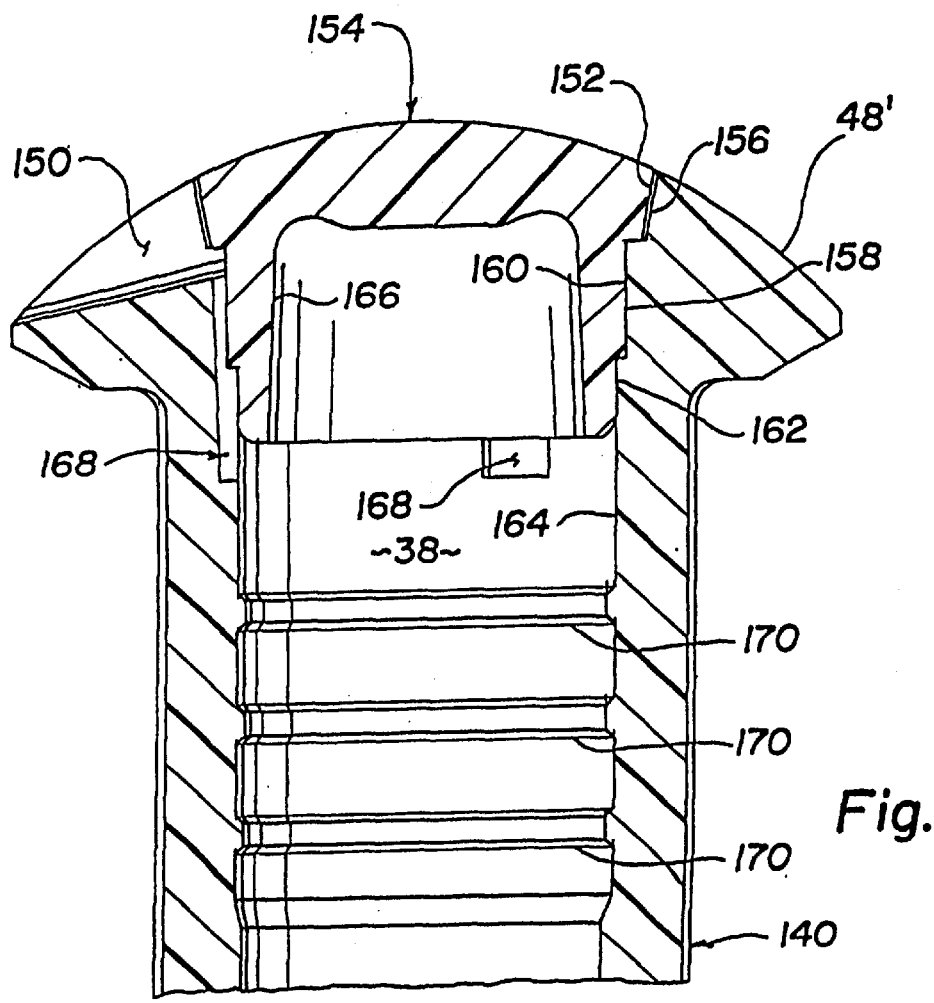
FIG. 11 is a cut away elevational view of the structure at the back end of the plunger and end cap of FIG. 9 and 10 along line 11—11 showing the preferred closure.

FIG. 10 shows an enlarged top plan view illustrating the use of three channels 150 in combination with a preferred closure 154 installed in circular opening 152. FIG. 11 best shows how the channels 150 receive vented air from hollow interior 38. Closure 154 preferably has a stepped outer surface comprising a rear step 156 which rests in opening 152, an intermediate step 158 which rests in an enlarged portion 160 of the inner side of wall 140 and a front step 162 which rests against inner surface 164 of wall 140. In effect, these structures provide convenient seating for closure 154. Steps 158 and 162 are conveniently provided in a downwardly depending skirt 166.

Importantly, inner surface 164 everywhere there is a channel 150, is provided with a longitudinally extending groove 168 in fluid communication with the hollow interior 38 and the channels 150. Any convenient number may be chosen as the channels are easily molded into the end cap when it is formed. The longitudinally extending grooves 168 do not extend through the entirety of the wall 140 although they could. They are designed for ease of molding since they can formed in the mold that makes the plunger without using separate pins to form an opening. This is an important cost consideration in a multiple out high speed molding process. This structure is designed for preventing the user's thumb from obstructing the vent opening leading from the interior of the plunger thereby assuring that venting will take place.

Figure 9:
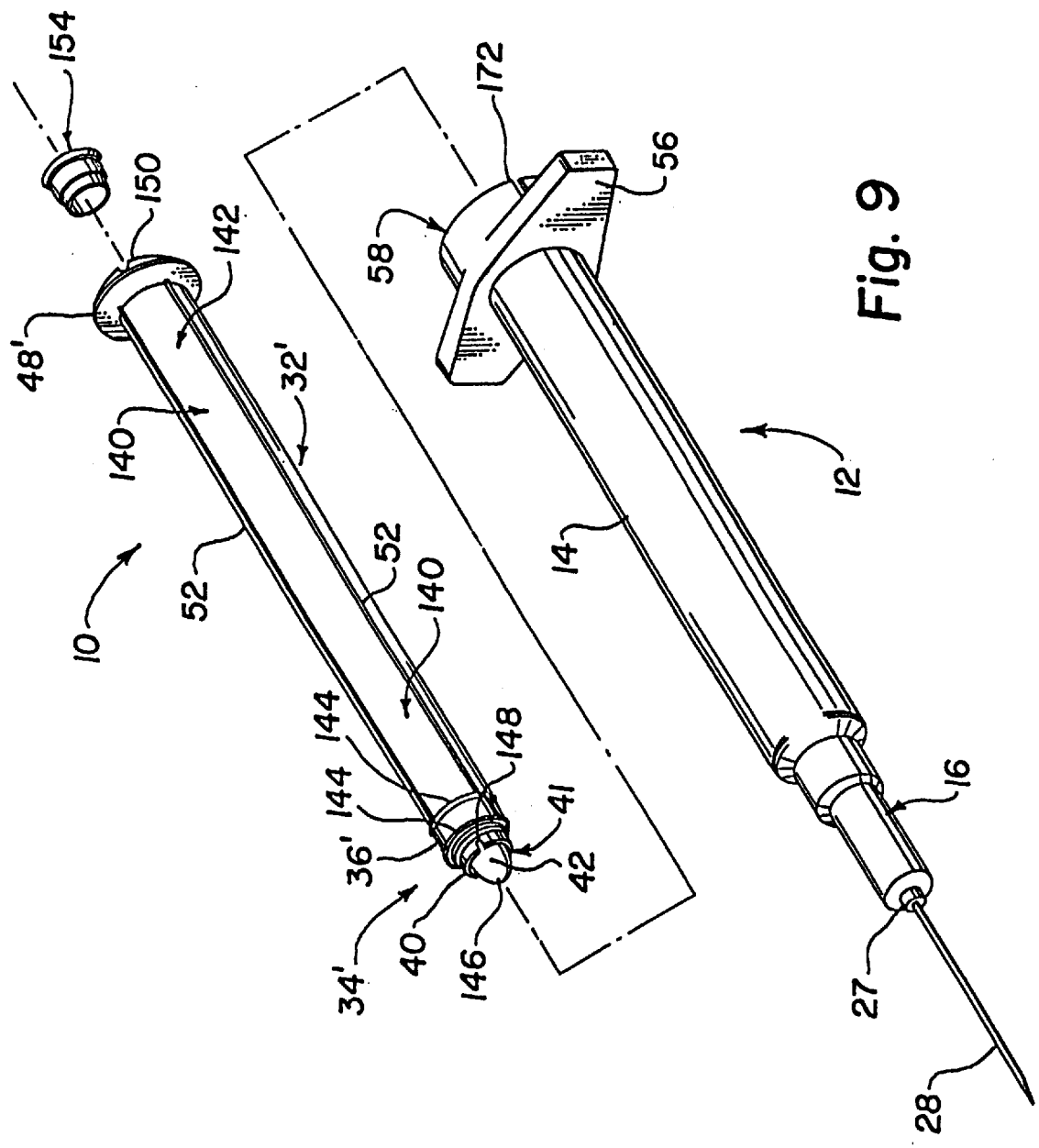
FIG. 9 is an exploded perspective view showing the barrel and retraction mechanism of FIG. 1 with a modified plunger assembly.
Figure 12:
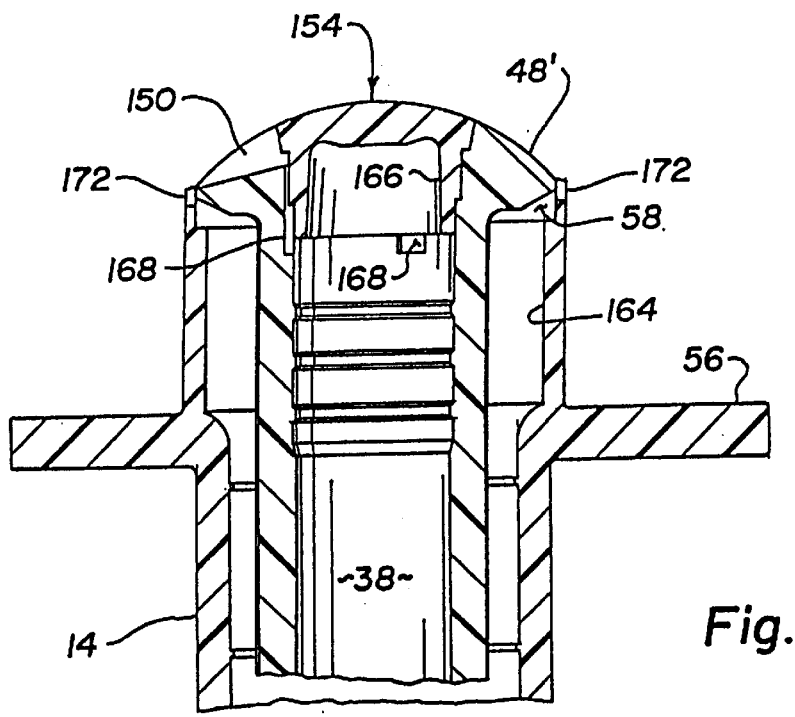
FIG. 12 is a cut away elevational view of the plunger end cap and closure of FIG. 11 as the thumb cap is just being received into the barrel opening.

Referring now to FIGS. 9 and 12, it will be noted that opening 58 in the back end of barrel 14 includes slots 172 in fluid communication with the hollow interior of the plunger through one or more channels 150 so that when thumb cap 48' is received in opening 58, no seal is created by the thumb being in contact with opening 58 which might otherwise prevent air from venting. The outer periphery of thumb cap 48' is closely received in opening 58 as the syringe is fired, to prevent reuse. Thumb cap 48' is preferably sized in relation to barrel 14 such that opening 58 is simply an extension in a linear direction of the wall of barrel 14 rather than enlarged as shown. Finally, the interior surface 164 preferably has several annular constrictions 170 designed to catch the head of stopper 42 during its rearward travel. Since stopper 42 is preferably installed from the rear of the plunger before closure 154 is put in place, the constrictions 170 must allow stopper 42 to be forced through to the front.

Figure 13:
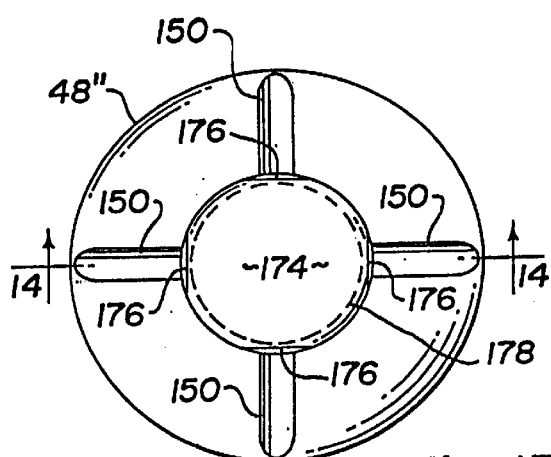
FIG. 13 is a plan view of a first alternative thumb cap and closure combination utilizing a flat sided closure and four channels in the thumb cap.
Figure 15:
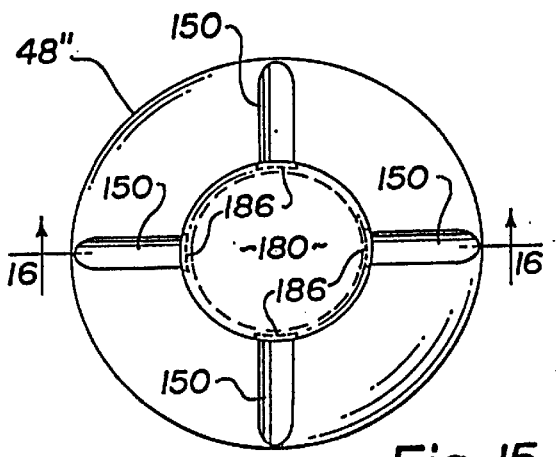
FIG. 15 is a plan view of a second alternate thumb cap and closure combination with four channels in the thumb cap and undercut portions to provide a vent passage.
Figure 14:
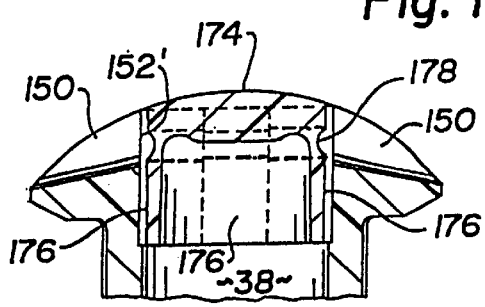
FIG. 14 is a cut away elevational view on the lines 14—14 of the thumb cap closure combination of FIG. 13.
Figure 16:
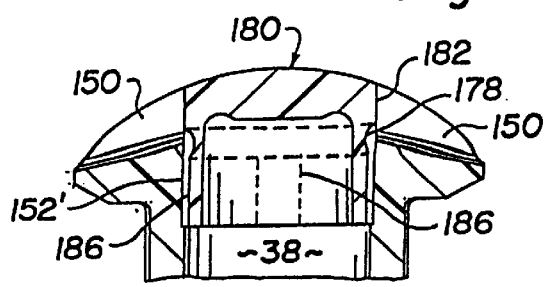
FIG. 16 is a cut away elevational view on the lines 16—16 of the combination of FIG. 16.

A first alternative thumb cap and closure arrangement is illustrated in FIGS. 13 and 14. In this embodiment, four channels 150 are provided in thumb cap 48". Closure 174 has four flat side portions 176 spaced around the periphery at 90° intervals, each in fluid communication with a channel 150. A gap is created at each flat side between the flat sides 176 and the opening 152' which are in fluid communication with interior 38 to create a flow passage for air from interior 38 through the gap along the flat side then into channel 150. Annular groove 178 in closure 174 may be used to fluidly connect each of the flat areas 176 at the level of channels 150. In addition to equalizing air flow, the annular groove allows venting of air regardless of the angular orientation of closure 174 with respect to thumb cap 48".

A second alternate embodiment has the same thumb cap 48" with a modified closure 180. Closure 180 has a head 182 which snugly fits within opening 152' which is at the back of the plunger. Opening 152' is only slightly larger than the interior of the plunger to provide a seat for the closure. Four undercut portions 186 are each in joint fluid communication with the interior 38 and one of the channels 150 to create a flow passage from the interior 38. Closure 180 effectively seals the opening 152' so that no fluid particles can escape from the opening. As in the previous embodiment, an annular groove 178 bridges each undercut portion opening into a corresponding channel 150 thereby tying the undercut portions together in fluid communication regardless of the angular orientation of the parts.

In operation, there are many advantages to the improved combination disclosed herein. The diameter of the stopper in both embodiments and the slidable retaning ring member in the first embodiment, in relation to the diameter across the fluid chamber, makes it possible to produce a syringe which withstands high blowout pressure. By minimizing the effective surface area exposed to the pressurized fluid during an injection, the syringe will withstand injection thumb force of around fifteen to eighteen pounds during injection and at the same time retract in response to as little as five to six pounds of force on the plunger once the injection fluid has been injected. Once the fluid has been injected, cumulation of force required to concurrently operate the retraction mechanism is avoided. First the stopper is moved back and then the needle holder is released. By constricting the diameter of the syringe near a transition zone where the nose begins, a constriction enables the needle holder to be smaller which in turn allows it to fit in a smaller opening with a smaller stopper in the retraction cavity of the hollow plunger.

A vacuum must be pulled in order to fill the syringe. The ring member or the needle holder, as the case may be, must seal the front nose of the syringe body because otherwise vacuum could be lost and fluid could enter the spring area and leak out the front. The hollow outer body and syringe plunger are preferably made from conventional plastic material used for syringes, which has some flexibility. The tolerances on the diameter of mating facing surfaces between the head of the needle holder and the barrel and between the stopper and head of the plunger are not critical in order to maintain a consistent holding and dislodging force. This is believed to be because increasing interference fit increases the frictional holding force only up to a point and then the surrounding wall simply expands a small amount or the internal parts are compressed a small amount without a corresponding increase in the longitudinal force required to move the retainer member or plug member in the retraction direction. It is a desirable self correcting mechanism which is a cost and quality benefit in making the parts. It is believed that a plastic retainer member could be used and the same self limiting frictional holding force would be obtained.

In the best mode the stopper and the ring member are preferably made from a thermoplastic rubber material designated number 181-55 available from Advanced Elastomer Systems, 540 Maryville Centra Drive, St. Louis, Mo. and sold under the trade name Santoprene®. It is said to have a characteristic hardness around 55 on the Shore A durometer scale which allows for the right amount of resistance to compression, fluid resistance such that the material does not swell when in contact with most fluids, environmental stability allowing the friction and sealing properties to remain non-temperature sensitive, good property retention after aging and excellent property retention after sterilization by all accepted methods. The plunger seal around the head of the plunger is conventional.

The parts are few in number and easily mass produced. The alternate embodiment has the fewest number of separate parts of any tamperproof retractable syringe. The plunger has a one piece hollow outer body with a transition zone and a narrow nose portion. The internal diameter is stepped to greater diameters from front to back for molding around a non-collapsible core which can be extracted from the rear. The same is true for the plunger.

Assembly is greatly simplified and can be accomplished with high speed mechanized equipment. The needle holder and spring are installable from the rear of the barrel without the needle. In the first embodiment the retainer member is forced fit over the inner head of the needle holder and the assembly together with the uncompressed spring are pushed forward and held by sliding engagement of the cooperating inwardly and outwardly facing surfaces while compressing the spring. The front of the needle holder passes through an opening in the nose which makes it easy to install the needle from the front by conventional means. The alternate embodiment is installed the same way except that there is no separable retainer member around the head of the needle holder.

The narrow nose provides a particular advantage for mechanized assembly. The nose has a wall defining an elongated internal cavity which closely confines the spring and needle holder combination. During installation this cavity serves as a guide to steer the needle holder and uncompressed spring into a compressed state of the spring. This solves an important assembly problem. If there is much lateral space in the nose around the spring, when the uncompressed spring is being compressed, it is a laterally unstable column which flexes sideways and bunches up causing a jam up. It might be added that rounded edges on the bottom of the slot directly below retainer 66 would further facilitate entry of the end of the spring.

The stopper is also installable from the rear of the plunger by pushing it forward until the cooperating lands are slidingly engaged. Then plug member 50 is force fit or otherwise fixed in the opening at the back of the plunger and the plunger is installed in the outer body. It is not necessary to try to pass the sharp needle through an elongated body with constricted openings where slight misalignment could cause hangups. The head of the needle holder simultaneously acts as a seal as well as a holding device such that no seal is required at the tip of the nose and no ultrasonic welding of separate parts is required.

There is no necessity for using internal locking teeth of any kind. No locking teeth are needed to hold the retraction mechanism or to lock the plunger after retraction. Locking teeth present difficult molding and quality control problems, tend to be temperature sensitive and tend to require a larger diameter barrel which increases premature blowout problems. In addition to the non-reusability provided by separation of the retainer ring from the head of the needle holder and dislodgement of the stopper, the plunger is not accessible after retraction because it is depressed within an opening at the back of the outer body. This additional tamperproof feature is provided in a one piece body without the necessity for hooking anything or twisting anything. The easily made and installed force fit plug at the back of the retraction cavity prevents access to the retracted components. The Federal government has rights in the invention under 35 U.S.C. §203. The Federal government has a nonexclusive, nontransferable irrevocable, paid up license to the invention as set forth in the priority documents.

I claim:

1. A syringe plunger handle assembly for use in a syringe barrel to inject fluid, comprising:

an elongated plunger formed with a longitudinally extending generally tubular wall defining a hollow interior along the length of the plunger, the plunger having a head end in front and a rear end portion with a thumb cap behind;

the outer side of the wall at the head end has a plunger seal adapted to slide in sealed contact with a tubular wall when the plunger is moved within a syringe barrel;

the wall at the head end of the plunger has a reduced diameter front portion extending forwardly beyond the plunger seal to a tip at the front of the plunger defining an opening within the front end portion leading into the hollow interior, the wall behind the tip having a stepped inner side surface comprising a land having an inwardly facing surface and a larger diameter portion extending behind the land into the hollow interior;

a separate dislodgeable stopper slidingly held within the reduced diameter front portion of the plunger head by a holding force in excess of an expected fluid injection pressure force during use of the plunger in a syringe barrel, the stopper having a back end portion comprising a land and a reduced diameter front end portion extending a fixed distance forwardly beyond the tip, the stopper land having an outwardly facing surface in sliding sealed engagement with the inwardly facing surface of the land in the plunger wall, said lands comprising cooperating lands which apply said holding force to the stopper and seal the hollow interior of the plunger from said expected fluid injection pressure force; and the cooperating lands have sufficient length to allow the dislodgeable stopper to move said fixed distance back to the tip in sliding response to forward movement of the plunger after the front of the stopper contacts a stop, whereby said holding force is reduced by substantial disengagement of the cooperating lands in preparation for dislodgement of the stopper without unsealing the hollow interior of the plunger.

2. The syringe plunger handle assembly of claim 1 wherein a vent for the hollow interior is located at the rear end portion of the plunger.

3. The syringe plunger handle assembly of claim 2 wherein the thumb cap at the rear end portion of the plunger is provided with a channel which receives vented air from the hollow interior.

4. The syringe plunger handle assembly of claim 3 wherein said vent comprises at least one groove at the rear end portion of the plunger in fluid communication with said channel for venting the retraction cavity in the plunger.

5. The syringe plunger handle assembly of claim 1 wherein the thumb cap at the rear end portion of the plunger surrounds an opening suitable for installation of the dislodgeable stopper into the hollow interior and a closure for the opening in the thumb cap.

6. The syringe plunger handle assembly of claim 5 wherein at least one channel in the thumb cap receives vented air from the hollow interior.

7. The syringe plunger handle assembly of claim 6 wherein the closure has at least one cutaway side portion in joint fluid communication with the hollow interior and said channel to create a vent passage.

8. The syringe plunger handle assembly of claim 7 wherein the rear end portion of the plunger has an internal surface with at least one groove in fluid communication with the hollow interior and said at least one channel in the thumb cap.

9. The syringe plunger handle assembly of claim 5 wherein the closure has a headed portion fitted in the opening in the thumb cap and a skirted side containing an undercut configured to reside in fluid communication jointly with the hollow interior and at least one channel in the thumb cap to comprise at least one vent passage from the hollow interior.

10. A syringe plunger handle assembly and syringe barrel combination for use in a retractable syringe for injecting fluids, comprising:
a hollow syringe body having an elongated tubular wall comprising an elongated barrel portion having an open back end;
an elongated plunger disposed for reciprocation in sliding sealed contact with the barrel portion of the body, the plunger having a tubular wall defining a head portion in front, a back end portion carrying a thumb cap and hollow interior comprising a retraction cavity located between the head portion and thumb cap;
the thumb cap having an outer side adapted to reside in close association with the open back end of the plunger barrel when the plunger is nearly fully depressed; and
the plunger having a vent in fluid communication with the retraction cavity, to allow airflow from the retraction cavity.

11. The combination of claim 10 wherein the vent in fluid communication with the retraction cavity is located at the rear end portion of the plunger.

12. The combination of claim 11 wherein said vent is an opening in the wall of the plunger.

13. The combination of claim 11 wherein the thumb cap at the rear end portion of the plunger is provided with a channel which receives vented air from the retraction cavity.

14. The combination of claim 11 wherein the thumb cap at the rear end portion of the plunger is provided with a groove which receives vented air from the retraction cavity.

15. The combination of claim 13 wherein said vent comprises at least one groove at the rear end portion of the plunger in fluid communication with said channel for venting the retraction cavity in the plunger.

16. The combination of claim 15 wherein the back end portion of the barrel of the syringe body includes at least one slot which allows vented air to escape without being trapped by a user's thumb during retraction when the thumb cap is pressed down.

17. The combination of claim 10 wherein the thumb cap at the rear end portion of the plunger surrounds an opening in the thumb cap and has a closure for the opening in the thumb cap.

18. The combination of claim 17 wherein said vent is an opening in the wall of the plunger.

19. The combination of claim 17 wherein at least one channel in the thumb cap receives vented air from the retraction cavity.

20. The combination of claim 19 wherein the closure has at least one cutaway side portion in joint fluid communication with the retraction cavity and said channel to create a vent passage.

21. The combination of claim 20 wherein the rear end portion of the plunger has an internal surface with at least one groove in fluid communication with the retraction cavity and said at least one channel in the thumb cap.

22. The combination of claim 19 wherein the closure has a headed portion fitted in the opening in the thumb cap and a skirted side containing an undercut configured to reside in fluid communication jointly with the retraction cavity and at least one channel in the thumb cap to comprise at least one vent passage from the retraction cavity.

23. The combination of claim 19 wherein the back end portion of the barrel of the syringe body includes at least one slot which allows vented air to escape without being trapped during retraction when the thumb cap is pressed down.

24. A syringe plunger handle assembly for a retractable syringe, comprising:
a hollow syringe body having a longitudinally extending tubular wall comprising an elongated barrel portion having an open back end;
an elongated plunger having a head portion in front slidingly mounted for reciprocation within the hollow syringe body;
the plunger having a tubular wall defining the head portion in front, a rear end portion in back terminating in a thumb cap and a retraction cavity therein;
a dislodgeable stopper insertable through an opening in the thumb cap for installation within the head portion at the front of the plunger; and
a closure installable in the thumb cap wherein said end portion is vented to allow air flow to or from the retraction cavity.

25. A tamperproof retractable syringe structure designed for one use, comprising:
a hollow syringe body comprising a syringe barrel having an open back end, the barrel having a front end portion containing a retraction mechanism configured for operation by a plunger;
a plunger reciprocatably mounted in sliding sealed contact with the barrel, the plunger having a thumb cap at its back end for working the plunger relative to the barrel and a front end configured to operate the retraction mechanism;
the plunger having a tactile first position felt by a user pressing the thumb cap at the end of free travel of the plunger in the barrel when the plunger is moved forward to a stop, the plunger having a length relative to the length of the barrel whereby in the tactile first position of the plunger a portion of the plunger and the thumb cap extend behind the barrel for grasping in order to draw fluid into the barrel by partially withdrawing the plunger from the barrel;

the plunger having a retraction position obtained by pressing the thumb cap to move the plunger forward beyond the tactile first position and thereby operating the retraction mechanism and simultaneously lodging the thumb cap in the open back end of the barrel thereby rendering the thumb cap inaccessible for grasping.

26. The tamperproof retractable syringe of claim 25 wherein the thumb cap has a periphery slightly smaller than an opening at the back end of the barrel to frustrate efforts to remove the plunger from the barrel.

27. The tamperproof retractable syringe of claim 26 wherein the back end of the barrel does not resist entry of the thumb cap when the plunger is moved forward to the retraction position.

28. The tamperproof retractable syringe of claim 27 wherein entry of the thumb cap into the opening at the back end of the barrel is not accompanied by locking of the plunger in the barrel.

29. The tamperproof retractable syringe of claim 27 wherein the thumb cap reversibly enters the opening at the back end of the barrel.

30. The tamperproof retractable syringe of claim 26 wherein the opening at the back end of the barrel is adapted to receive the thumb cap freely without adding another component of retraction triggering force to overcome as the plunger is moved forward from the tactile first position to the retraction position.

31. The tamperproof retractable syringe of claim 26 wherein the opening at the back end of the barrel is configured as a stop which contacts the thumb cap after the thumb cap enters the opening to prevent further forward movement of the plunger.

32. The tamperproof retractable syringe of claim 31 wherein the back end of the barrel is radially enlarged relative to the barrel with a correspondingly larger opening at the back of the barrel and a correspondingly larger close fitting thumb cap than a syringe without said enlargement.

33. The tamperproof retractable syringe of claim 25 wherein the front end of the plunger has a closure which acts as the stop for the plunger when the plunger is moved forward to the tactile first position.

34. The tamperproof retractable syringe of claim 29 wherein the front end of the plunger has a closure which acts as the stop for the plunger when the plunger is moved forward to the tactile first position.

35. The tamperproof retractable syringe of claim 30 wherein the front end of the plunger has a closure which acts as the stop for the plunger when the plunger is moved forward to the tactile first position.

36. The tamperproof retractable syringe of claim 35 wherein the retraction mechanism comprises a needle holder held in an unretracted position by a removable ring member.

37. The tamperproof retractable syringe of claim 36 wherein the ring member is removed from the needle holder in response to movement of the plunger to the retraction position.

38. The tamperproof retractable syringe of claim 37 wherein the front end of the plunger has a closure which acts as the stop for the plunger when the plunger is moved forward to the tactile first position.

39. The tamperproof retractable syringe of claim 37 wherein the front end portion of the barrel comprises a nose portion of reduced diameter relative to the barrel, the nose portion principally containing the retraction mechanism.

40. The tamperproof syringe of claim 39 wherein the needle holder is grounded against forward movement in the nose of the syringe.

41. A tamperproof retractable syringe structure designed for one use, comprising:

a hollow syringe body having a barrel having an open back end and a nose portion in the front of the barrel;

a plunger operated retraction mechanism lodged in the nose portion of the barrel;

an elongated plunger handle disposed for reciprocation in the barrel, the plunger handle having a front portion slidingly sealing the barrel to form a variable fluid chamber above the retraction mechanism, the plunger having a thumb cap with a diameter slightly less than the diameter of the open back end;

the plunger having a tactile first pre-injection position which is felt by moving the plunger forward until it stops without operating the retraction mechanism, leaving a portion of the plunger handle and the thumb cap positioned a sufficient distance behind the barrel for gripping to partially withdraw the plunger when filling the syringe with fluid;

the plunger having a second position obtained by returning the plunger to the first pre-injection position to substantially empty the syringe then moving the plunger forward to a retraction position beyond the tactile first pre-injection position thereby operating the retraction mechanism and simultaneously lodging the thumb cap within the open back end of the barrel where it becomes inaccessible.

* * * * *

UNITED STATES PATENT AND TRADEMARK OFFICE
CERTIFICATE OF CORRECTION

PATENT NO : 6,090,077
DATED : July 18, 2000
INVENTOR(S) : Thomas J. Shaw

It is certified that error appears in the above-identified patent and that said Letters Patent are hereby corrected as shown below:

Col. 22, line 1
  replace "Claim 35"
  with --Claim 25--.

Signed and Sealed this

Twenty-fourth Day of April, 2001

Attest:

NICHOLAS P. GODICI

Attesting Officer

Acting Director of the United States Patent and Trademark Office